US006969524B1

(12) United States Patent
Tabata et al.

(10) Patent No.: US 6,969,524 B1
(45) Date of Patent: Nov. 29, 2005

(54) INTERFERON COMPLEX AND MEDICINAL USE THEREOF

(75) Inventors: Yasuhiko Tabata, Uji (JP); Saburo Sone, Kamakura (JP); Mayumi Seto, Kamakura (JP); Miyuki Sato, Kamakura (JP)

(73) Assignee: Santen Pharamceutical Co., Ltd., Osaka (JP)

( * ) Notice: Subject to any disclaimer, the term of this patent is extended or adjusted under 35 U.S.C. 154(b) by 276 days.

(21) Appl. No.: 10/110,420

(22) PCT Filed: Oct. 12, 2000

(86) PCT No.: PCT/JP00/07066

§ 371 (c)(1),
(2), (4) Date: Apr. 11, 2002

(87) PCT Pub. No.: WO01/26677

PCT Pub. Date: Apr. 19, 2001

(30) Foreign Application Priority Data

Oct. 12, 1999 (JP) .................................. 11/289178

(51) Int. Cl.[7] .............................................. A61F 2/02
(52) U.S. Cl. ...................................................... 424/423
(58) Field of Search ........................................ 424/423

(56) References Cited

U.S. PATENT DOCUMENTS 4,041,152 A    8/1977   Chany et al.

5,382,657 A    1/1995   Karasiewicz et al.

FOREIGN PATENT DOCUMENTS

| EP | 0 123 291 A2 | 10/1984 |
| JP | 6-192300 A | 7/1994 |
| WO | WO 95/13090 A | 5/1995 |
| WO | WO 97/18832 A | 5/1997 |
| WO | WO 99/32139 A | 7/1999 |
| WO | WO 99/32140 A | 7/1999 |

OTHER PUBLICATIONS

Y. Tabata et al, "Targeting of tumor necrosis factor to tumor by use of dextran and metal coordination", *J. Controlled Release*, vol. 59, No. 2, pp. 187-196 & cover page (1999).

Okushin et al, *Liver*, vol. 36, p. 735 (1995) (with English language Abstract).

Y. Tabata et al, "Simple Mixing of IFN with Polysaccharide Having High Liver Affinity Enables IFN to Target to the Liver", *J. Interferon and Cytokine Research*, vol. 19, pp. 287-292 (1999).

(Continued)

*Primary Examiner*—Carlos A. Azpuru
(74) *Attorney, Agent, or Firm*—Frishauf, Holtz, Goodman & Chick, P.C.

(57) ABSTRACT

An object of the present invention is to provide modified IFN so that duration of IFN in blood is prolonged and IFN acts specifically on tissues having neovasculature, particularly tumors or ophthalmic tissues having neovasculature. The present invention provides an interferon-dextran complex obtained by mixing interferon with dextran having chelate ligands in the presence of a metal ion.

18 Claims, 1 Drawing Sheet

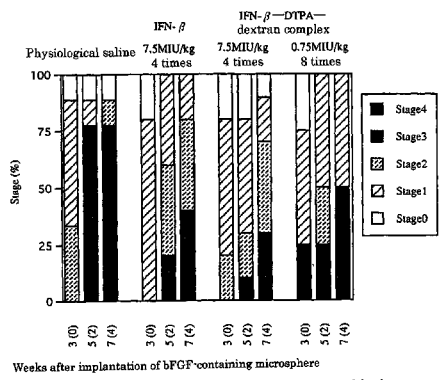

Inhibitory effect on angiogenesis of IFN-β-dextran complex

Classification of degree by fluorescent fundus photography (degree and potency of fluorescence leakage)
Stage 0: No fluorescence leakage
Stage 1: Topical slight fluorescence leakage + (same level as background choroidal vessel)
Stage 2: Topical fluorescence leakage ++ (stronger than background)
Stage 3: Moderate fluorescence leakage (fluorescence leakage ++)
Stage 4: Fluorescence leakage over wide range (fluorescence leakage ++)

OTHER PUBLICATIONS

Y.A. Sidky et al, "Inhibition of Angiogenesis by Interferon: Effects on Tumor- and Lymphocyte-induced Vascular Responses", *Cancer Res.,* vol. 47, pp. 5155-5161 (Oct. 1987).

W.E. Fung, "Interferen Alpha 2a for Treatment of Age-Related Macular Degeneration", *Am. J.Ophthalmology,* vol. 112, No. 3, pp. 349-350 (1992).

J.W. Miller et al, "Regression of Experimental Iris Neovascularization with Systemic Alpha-interferon", *Ophthamology,* vol. 100, No. 1, pp. 9-14 (1992).

J. Wakelee-Lynch, "Interferon May Offer First Drug Therapy for Diabetic Retinopathy", *Diabetes Care,* vol. 15, No. 22, pp. 300-301 (Feb. 1992).

T. Yamaoka et al, "Body Distribution Profile of Polysaccharides after Intravenous Administration", *Drug Delivery,* vol. 1, pp. 75-82 (1993).

Fig. 1

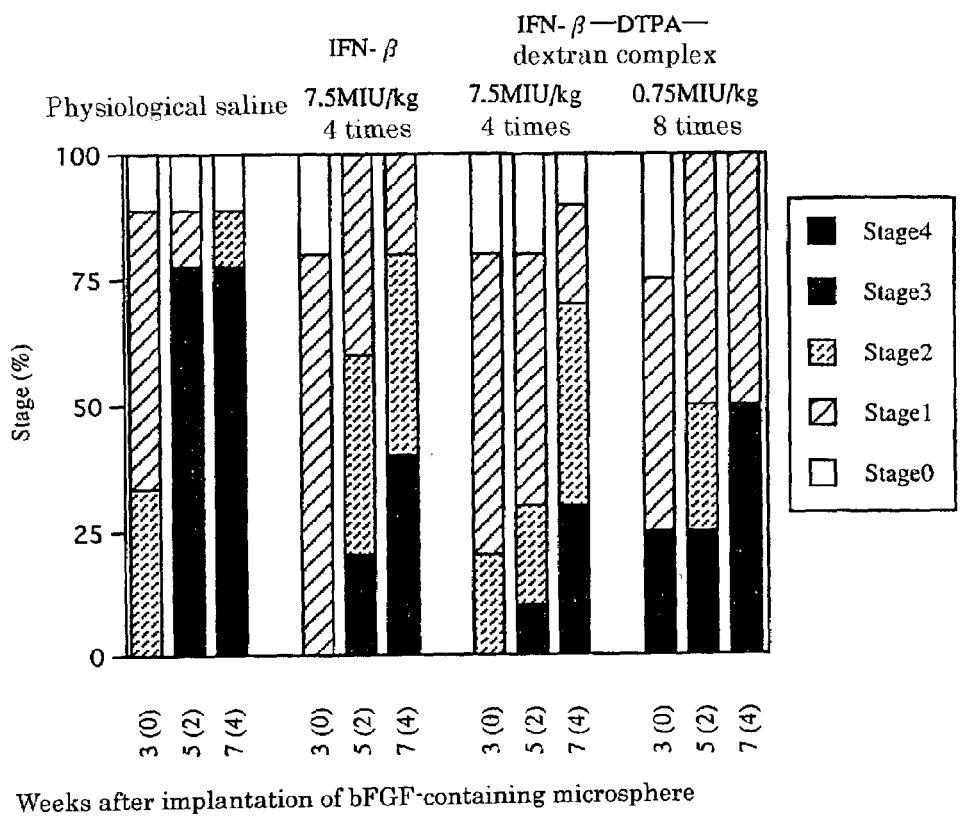

Weeks after implantation of bFGF-containing microsphere

*The values in the parentheses are weeks after administration of the drug.

Inhibitory effect on angiogenesis of IFN-β-dextran complex

Classification of degree by fluorescent fundus photography (degree and potency of fluorescence leakage)

Stage 0: No fluorescence leakage

Stage 1: Topical slight fluorescence leakage + (same level as background choroidal vessel)

Stage 2: Topical fluorescence leakage ++ (stronger than background)

Stage 3: Moderate fluorescence leakage (fluorescence leakage ++)

Stage 4: Fluorescence leakage over wide range (fluorescence leakage ++)

INTERFERON COMPLEX AND MEDICINAL USE THEREOF

This application is a United States national phase application under 35 USC 371 of International Application No. PCT/JP00/07066 filed Oct. 12, 2000.

TECHNICAL FIELD

The present invention relates to an interferon-dextran complex being a novel administration system of interferon, a process for producing the same, pharmaceutical use thereof and a method of prolonging duration of interferon in blood by forming the interferon-dextran complex.

BACKGROUND ART

Interferon (IFN) is a drug having extensive biological effects such as an antiviral effect, an antitumor effect and an immune regulatory effect and is used for treatment of various malignant neoplasms, treatment of diseases owing to viral infection and the like. However, since IFN has a short in vivo half-life, administration of IFN alone does not give sufficient expected efficacy. At present, when IFN-β is used for treatment of chronic hepatitis C, it is administered once a day every day. In recent years, however, it was reported that efficacy of IFN-β is enhanced by administering IFN-β not once a day but twice a day in a half dose (Okushin et al., Liver, Vol. 36, p. 735, 1995). Accordingly, it is considered that it is important to maintain a blood concentration of IFN in order to develop the efficacy of IFN. Namely, it is desirable to increase in vivo stability of IFN and to maintain the blood concentration of IFN. Modification of IFN with macromolecular materials has been made so far for this purpose. For example, an IFN-polyethylene glycol (PEG) conjugate having an enhanced in vivo half-life of IFN was reported (Japanese Laid-open Patent Publication No. 192300/1994). However, its clinical utility is unknown at the present time. Accordingly, an IFN preparation having increased in vivo stability and a maintained blood concentration is desired.

On the other hand, it is also important to make IFN act on a target site specifically for improving the efficacy of IFN (i.e. targeting of a drug). Modification of IFN with macromolecular materials has been made so far for this purpose. For example, an IFN-α-pullulan conjugate increasing accumulation (targeting) of IFN to a liver (Tabata, Y. et al., J. Interferon and Cytokine Research, 19, 287–292, 1999) was reported.

It was reported that IFN has an inhibitory effect on angiogenesis, and its effectiveness for tumor-induced neovasculature was also reported (Sidky, Y. A. et al., Cancer Res., 47, 5155–5161, 1987). Further, its effectiveness was reported for age-related macular degeneration (Fung, W. E., Am. J. Ophthalmol., 112, 349, 1991), neovascular glaucoma (Miller, J. W. et al., Ophthalmology, 100, 9, 1992), diabetic retinopathy (Wakelee-Lynch, J. and Banks, P., Diabetes Care, 15, 300, 1992) and the like in diseases in an ophthalmological field.

As mentioned above, however, since IFN has short duration in blood and has no organ specificity either, free IFN does not exhibit sufficient effects expected as an angiogenesis inhibitor. Accordingly, it is necessary to modify IFN in some degree so that the duration of IFN in blood is prolonged and IFN acts specifically on tissues having neovasculature, particularly tumors or ophthalmic tissues having neovasculature.

Though the above-mentioned IFN-α-pullulan conjugate increases the accumulation (targeting) of IFN in the liver, the conjugate is not formed so that IFN exhibits the inhibitory effect on angiogenesis sufficiently, namely IFN acts specifically on the tissues having neovasculature, particularly the tumors or theophthalmic tissues having neovasculature. Though pullulan increases in vivo half-life, it has short duration in blood since it tends to accumulate in a liver (Yamaoka, T. et al., Drug Delivery, 1, 75–82, 1993). However, this feature does not make IFN exhibit the inhibitory effect on angiogenesis sufficiently.

An object of the present invention is to provide modified IFN so that the duration of IFN in blood is prolonged and IFN acts specifically on the tissues having neovasculature, particularly the tumors or the ophthalmic tissues having neovasculature.

DISCLOSURE OF THE INVENTION

Studying precisely in order to solve the above-mentioned problems, the present inventors found that in vivo stability of IFN, particularly stability of IFN in blood is improved by mixing IFN with dextran having chelate ligands in the presence of a metal ion to form an IFN-dextran complex and found that IFN accumulates in tissues having neovasculature, particularly tumors or ophthalmic tissues having neovasculature and enhances an inhibitory effect on angiogenesis to complete the present invention.

Namely, the present invention provides the interferon-dextran complex which can be obtained by mixing interferon with dextran having the chelate ligands in the presence of the metal ion. The present invention provides a pharmaceutical comprising the present interferon-dextran complex as an active ingredient, and the pharmaceutical can be used, for example, as an angiogenesis inhibitor. The present invention provides a method of inhibiting angiogenesis comprising administering a required amount of the present interferon-dextran complex or a composition comprising this complex and a pharmacologically acceptable carrier or excipient to a patient. The present invention provides use of the present interferon-dextran complex as the angiogenesis inhibitor. The present invention further provides a method of prolonging duration of interferon in blood comprising mixing interferon with dextran having the chelate ligands in the presence of the metal ion to form the interferon-dextran complex. Further, the present invention provides a process for producing the interferon-dextran complex comprising mixing interferon with dextran having the chelate ligands in the presence of the metal ion.

As mentioned above, the present interferon-dextran complex can be obtained by mixing interferon with dextran having the chelate ligands in the presence of the metal ion.

Interferon contained in the present complex can be any of α-type, β-type, γ-type, consensus type and hybrid type and can be any of natural type, genetic recombination type and chemical synthesis type with respect to its origin. It was reported that IFN-α and IFN-β share a receptor and have similar effects, but IFN-β has higher efficacy than IFN-α with regard to the inhibitory effect on angiogenesis (Sidky, Y. A. et al., Cancer Res., 47, 5155–5161, 1987). Accordingly, IFN-β is preferably used.

Dextran having a molecular weight of 4,000 to 500,000 is usually used, and dextran having a molecular weight of 70,000 to 500,000 is preferably used in the present invention.

The chelate ligand introduced into dextran chemically can be any ligand having plural groups which can coordinate the metal ion and having a chemical structure which can chelate the metal ion by coordinating the metal ion with these plural groups. Examples of the group which can coordinate the metal ion are carboxyl, carbonyl, cyano, amino, imidazolyl, thiol, hydroxyl and the like. Examples of compounds which have these plural groups and can chelate the metal ion are complexone ligands such as iminodiacetic acid, nitrilotriacetic acid, ethylenediaminetetraacetic acid, diethylenetriaminepentaacetic acid (DTPA), triethylenetetraminehexaacetic acid, N-hydroxyethylethylenediaminotriacetic acid, ethylene glycol diethyl etherdiaminetetraacetic acid and ethylenediaminetetrapropionic acid, diethylenetriamine, triethylenetetramine, α-amino acids (glutamic acid, lysine, aspartic acid, cystine, histidine, tyrosine, etc.) and the like. These chelate ligands can be introduced into dextran solely or in combination. In addition, it is also effective to introduce a 2,2'-dipyridine or 1,10-phenanthroline residue having excellent chelation ability into dextran.

These chelate ligands can easily be introduced into dextran by known various methods. For example, the chelate ligand can be introduced into dextran by forming a chemical bond between a hydroxyl group of dextran and an amino group of the chelate ligand by the cyanuric chloride method ("New Experimental Chemical Course", 19, Polymer Chemistry I, The Chemical Society of Japan), the cyanogen bromide method ("Biochemical Experimental Course", I, Chemistry of Protein I, The Biochemical Society of Japan), the epichlorohydrin method ("Experimental Chemical Course", 29, Macromolecular Material, 4th Ed., The Chemical Society of Japan) or the like. A bonding reaction by the periodate oxidation method ("Biochemical Experimental Course", 4, Chemistry of Succharide II, The Biochemical Society of Japan) is also effective. Further, it is possible to activate the hydroxyl group of dextran with carbonylimidazole and then bond the hydroxyl group with a carboxyl group or the amino group of the ligand. In addition to the above-mentioned bonding reactions, DTPA anhydride, an aminobenzyl or isothiocyanobenzyl derivative of EDTA and the like are preferable since they can easily react with the hydroxyl group of dextran by only mixing them at room temperature to introduce chelate ligands into dextran. In the above-mentioned respective methods, unreacted chelate ligands can be removed, for example, by dialysis against water.

In addition to the above-mentioned methods of introducing the ligand residues having chelation ability directly into dextran, a spacer can be introduced between the chelate ligand residue and dextran. For example, first, into dextran is introduced N,N'-bis(3-aminopropyl)-1,3-propanediamine, bis(3-aminopropyl)amine, aliphatic diamine having different carbon chain length, an ester derivative of lysine or the like, which has amino groups at both terminals. Then, the chelate ligand is introduced into one free terminal amino group to prepare dextran having the chelate ligand introduced through the spacer. In addition to the above-mentioned examples, it is also possible to use other spacer molecules having chemical reactive functional groups such as hydroxyl and carboxyl at both terminals of the molecules. Dextran having the chelate ligand residue introduced through the spacer can be synthesized by combining the above-mentioned reactions.

Metals to be used are not particularly limited if the metals are safe for living bodies. The metals can be those forming a stable chelate with the chelate ligand residue introduced into dextran, for example, transition metals and alkaline earth metals having a valency of bivalent or more and the like. Zinc, copper, nickel, cobalt and the like are preferable in view of stability of the metal chelate, bonding power with IFN and toxicity. There are many reports about biological toxicity of these metals ("Copper and Sanitation", published by Foundation Japan Copper Center, and the like). An $LD_{50}$ value of copper, which is considered to be extremely toxic, is more than 4,000 mg/kg (mouse, oral), and an $LD_{50}$ value of zinc is about 900 mg/kg (rat, intravenous injection). Each amount of copper and zinc to be used for the purpose of this study is about 1 to 1.5 mg/kg, which is 1/1000 or less as large as literature values. Accordingly, it is considered that biological toxicity of the metal ions to be used does not cause any problems. These metals are used to prepare the IFN-dextran complexes in the form of chlorides, sulfates, acetates or the like. These metal ions can be used solely or in combination.

The present interferon-dextran complex can be obtained by mixing interferon, the above-mentioned chelate ligand-introduced dextran and the above-mentioned metal ion. These three reactants can be mixed almost simultaneously. Alternatively, first, the chelate ligand-introduced dextran can be mixed with the metal ion to form a chelate compound, an unreacted metal ion can be removed by gel filtration chromatography or the like, and then the chelate compound can be mixed with interferon. In either case, a mixing temperature and a solvent are not particularly limited, the mixing temperature can be room temperature, and the solvent can be water.

When the three reactants are mixed almost simultaneously, mixing ratios of interferon, the chelate ligand-introduced dextran and the metal ion are not particularly limited. An interferon/dextran ratio is about 1/30,000 to 1/1, preferably about 1/3,000 to 1/30, and an interferon/metal ion ratio is about 1/4,000 to 10/1, preferably about 1/400 to 1/1 in weight ratios, expressed by ratios of interferon. At this time, a concentration of interferon in the mixture is, not particularly limited, usually 100,000 units/ml to 1,000,000,000 units/ml, preferably about 1,000,000 units/ml to 100,000,000 units/ml. Mixing time is not particularly limited, and can be about 5 to 150 minutes. In practice, it is not necessary to mix the three reactants completely at the same time. First optional two reactants can be mixed, and then the resulting mixture can be mixed with the remaining reactant as described in the following Example 1. After the reaction, it is preferable to remove unreacted metal ion and interferon by gel filtration chromatography or the like.

In a process wherein the chelate ligand-introduced dextran is first mixed with the metal ion to form the chelate compound, and then this compound is mixed with interferon, a mixing ratio of the chelate ligand-introduced dextran to the metal ion is, not particularly limited, about 1/10 to 1,000/1, preferably about 1/1 to 100/1 in a weight ratio. A concentration of the chelate ligand-introduced dextran in the mixture is usually about 0.1 mg/ml to 1,000 mg/ml, preferably about 1 mg/ml to 100 mg/ml. Mixing time is not particularly limited, and can be about 5 to 150 minutes. Next, an unreacted metal ion is removed by gel filtration chromatography or the like, and then the chelate compound is mixed with interferon. The mixing with interferon is not particularly limited, and the mixing can easily be carried out by adding a lyophilized mixture containing the chelate compound from which the unreacted metal ion is removed to an aqueous interferon solution. In this case, a ratio of interferon to the chelate compound, namely a dextran-metal complex is, not particularly limited, about 1/10,000 to 1/1, preferably about 1/4,000 to 1/10 in a weight ratio. At this time, an end concentration of interferon in the mixture is, not particularly limited, usually about 100,000 units/ml to 1,000,000,000 units/ml, preferably about 1,000,000 units/ml to 100,000,000 units/ml. Mixing time is not particularly limited, and the time can be about 5 to 150 minutes. Then, it is preferable to remove unreacted interferon by gel filtration chromatography or the like.

The present interferon-dextran complex can be used for treatment of various diseases by utilizing physiological activity of IFN. For example, the complex can be used for treatment of active chronic hepatitis B, chronic hepatitis C, other viral, diseases, various malignant neoplasms such as glioblastoma, medulloblastoma, astrocytoma and skin malignant melanoma, autoimmune diseases such as disseminated sclerosis and the like, and particularly the complex can be used as an angiogenesis inhibitor. Object diseases are those accompanied by angiogenesis, for example, inflammatory diseases such as nodose rheumatism and psoriasis, ophthalmopathy such as diabetic retinopathy, retinopathy of prematurity, angiogenesis glaucoma, Stevens-Johnson syndrome and analogous diseases thereof, ocular pemphigus and analogous diseases thereof, corneal burn or trachoma, cancers (mastocarcinoma, prostatic carcinoma, malignant melanoma, renal tumors, encephaloma, Kaposi's sarcoma and the like) and the like, preferably ophthalmopathy.

The dosage of the present complex is appropriately determined depending on age and body weight of patients, object diseases, symptoms, dosage form, administration route and the like. The dosage is generally in the range of 1,000 to 100,000,000 units/day, preferably in the range of 10,000 to 18,000,000 units/day.

The following Example 3 practically shows that the duration of interferon in blood can be prolonged by converting interferon into the interferon-dextran complex by the above-mentioned method. Accordingly, the present invention also provides the method of prolonging the duration of interferon in blood comprising mixing interferon with dextran having the chelate ligands in the presence of the metal ion to form the interferon-dextran complex.

The present IFN-dextran complex can be administered orally or parenterally as it is or in the form of a pharmaceutical composition obtained by mixing the complex with a known pharmacologically acceptable carrier, excipient or the like, and an intravenous injection is preferably used. Specific examples of dosage forms for oral administration are tablets, pills, capsules, granules, syrups, emulsions, suspensions and the like. These dosage forms are produced by known processes and contain a carrier or an excipient to be usually used in a preparation field. Examples of carriers and excipients for tablets are lactose, maltose, saccharose, starch, magnesium stearate and the like. Examples of dosage forms for parenteral administration are eyedrops, ointments, injections, fomentations, suppositories, pernasal absorbents, transpulmonary absorbents, percutaneous absorbents, local sustained release preparations and the like. Solution preparations can be prepared by known processes, for example, in a state where the IFN-dextran complex is embedded with liposome usually by dissolving the complex in a sterile aqueous solution used for an injection or suspending the complex in an extract and further emulsifying it. Solid preparations can be prepared by known processes, for example, in the form of lyophilized products by adding mannitol, trehalose, sorbitol, lactose, glucose or the like as the excipient to the IFN-dextran complex. Further, these preparations can also be powdered for use. These powders can also be mixed with polylactic acid, glycolic acid or the like and solidified for use. Gelling agents can be prepared by known processes, for example, in a state where the IFN-dextran complex is dissolved in a thickening agent or polysaccharide such as glycerin, polyethylene glycol, methyl cellulose, carboxymethyl cellulose, hyaluronic acid or chondroitin sulfate. In any preparations, human serum albumin, human immunoglobulin, α 2 macroglobulin, an amino acid or the like can be added as a stabilizer, and alcohol, sugar alcohol, an ionic surfactant, a nonionic surfactant can be added as a dispersant or an absorption promotor in the range not to impair physiological activity of IFN. A trace amount of a metal or an organic acid salt can also optionally be added.

BRIEF DESCRIPTION OF DRAWING

FIG. 1 is a graph showing comparison between an inhibitory effect on angiogenesis of the present interferon-dextran complex and an inhibitory effect on angiogenesis of free interferon studied in Example 2.

BEST MODE FOR CARRYING OUT THE INVENTION

The present invention is described more practically by giving Examples below.

EXAMPLE 1

Preparation of IFN-β-DTPA-Dextran

DTPA anhydride (22.4 mg, produced by Dojin Chemical Laboratory Co., Ltd.) and 4-dimethylaminopyridine (4.87 mg, produced by Nacalai Tesque Co., Ltd.) were added to an anhydrous dimethyl sulfoxide solution (10 ml) containing dextran (110 mg, molecular weight: 20,800, produced by Nacalai Tesque Co., Ltd.). This mixture was stirred at 40° C. for 24 hours to introduce a DTPA residue having chelation ability at a hydroxyl group of dextran. After the reaction, the reaction mixture was dialyzed against water for two days to remove DTPA which was not bonded to dextran, and the remainder was lyophilized to give dextran having a chelate ligand DTPA residue (DTPA-dextran) (yield: 80%, DTPA: 15 mol % by conductometric titration). Next, this aqueous DTPA-dextran solution (10 mg/0.153 ml) was added to an aqueous IFN-β (produced by Toray Industry, Inc.) solution (9 MIU/0.657 ml), and the mixture was stirred lightly at room temperature. Then, an aqueous $ZnCl_2$ solution (1.134 mg/0.09 ml (0.01 N HCl)) was added to the mixture, and the whole was stirred and allowed to stand at room temperature for 15 minutes to give a crude product. This crude product was gel filtrated with a Sephacryl S-200 (trade name) column to remove free IFN-3 and give a purified IFN-β-DTPA-dextran complex. A ratio of the IFN-β-DTPA-dextran complex to free IFN-β in the above-mentioned crude product was 70:30.

EXAMPLE 2

Inhibitory Effect on Angiogenesis of IFN-β-Dextran Complex

Choroidal neovasculature models were prepared according to the method of Kimura et al. (Invest. Ophthalmol. Vis. Sci., 36 (10), 2110–2119, 1995). Namely, a gelatin microsphere containing 100 μg of a basic fibroblast growth factor (bFGF) was injected into the subretinal space of pigmented house rabbit eyes. Fluorescent fundus photography was carried out on the 21st day after the bFGF injection, and retinal neovascularization was confirmed. The crude IFN-β-dextran complex (7.5 MIU/kg/day (total amount of IFN-β, the same meaning is applied to the following Example)) prepared in Example 1 or IFN-β (7.5 MIU/kg/day) was injected intravenously on the 22nd, 25th, 29th and 32nd days (total four times) after the bFGF injection. In addition, the crude IFN-β-dextran complex (0.75 MIU/kg/day) prepared in Example 1 was injected intravenously on the 22nd, 25th, 29th, 32nd, 36th, 39th, 43rd and 46th days (total eight times) after the bFGF injection. As a control group, physiological saline was administered similarly. Fluorescent fundus photography was carried out every week from the 3rd week to the 7th week after the bFGF injection, and crisis rates of neovasculature were measured to judge inhibitory effects.

Table 1 and FIG. 1 show that the IFN-β-dextran complex inhibited angiogenesis stronger than free IFN-β, comparing them in the same dose (7.5 MIU/kg/day, four times). Further, the IFN-β-dextran complex inhibited angiogenesis stronger than free IFN-β (7.5 MIU/kg/day, four times) even in a low dose (0.75 MIU/kg/day, eight times), i.e., the total dose was one fifth as high as that of IFN-β.

TABLE 1

Inhibitory effect on angiogenesis of IFN-β-dextran complex
Degrees are classified depending on intensity and potency of fluorescence leakage by fluorescent fundus photography.
Stage 0: No fluorescence leakage
Stage 1: Topical slight fluorescence leakage + (same level as background choroidal vessel)
Stage 2: Topical fluorescence leakage ++(stronger than background)
Stage 3: Moderate fluorescence leakage (fluorescence leakage ++)
Stage 4: Fluorescence leakage over wide range (fluorescence leakage ++)

|  |  | 3rd (0) week | 5th (2) week | 7th (4) week |
|---|---|---|---|---|
| Control (physiological saline administration) | 1 | 2 | 3(+1) | 4(+1) |
|  | 2 | 2 | 3(+1) | 4(+1) |
|  | 3 | 1 | 1(+0) | 2(+1) |
|  | 4 | 0 | 0(+0) | 0(+0) |
|  | 5 | 1 | 4(+3) | 4(+0) |
|  | 6 | 1 | 3(+2) | 4(+1) |
|  | 7 | 2 | 4(+2) | 4(+0) |
|  | 8 | 1 | 4(+3) | 4(+0) |
|  | 9 | 1 | 3(+2) | 4(+1) |
| Grade average |  | 1.22 | 2.77(+1.6) | 3.33(+0.6) |
| IFN-β administration 7.5 MIU/kg, 4 times | 1 | 1 | 1(+0) | 1(+0) |
|  | 2 | 1 | 2(+1) | 3(+1) |
|  | 3 | 0 | 1(+1) | 2(+1) |
|  | 4 | 1 | 4(+3) | 4(+0) |
|  | 5 | 1 | 2(+1) | 2(+0) |
| Grade average |  | 0.8 | 2(+1.2) | 2.4(+0.4) |
| IFN-β-dextran administration 7.5 MIU/kg, 4 times | 1 | 2 | 2(+0) | 2(+0) |
|  | 2 | 1 | 0(−1) | 0(+0) |
|  | 3 | 1 | 3(+2) | 4(+1) |
|  | 4 | 1 | 1(+0) | 3(+2) |
|  | 5 | 0 | 1(+1) | 1(+0) |
|  | 6 | 1 | 1(+0) | 2(+1) |
|  | 7 | 0 | 0(+0) | 1(+1) |
|  | 8 | 1 | 1(+0) | 2(+1) |
|  | 9 | 2 | 2(+0) | 3(+1) |
|  | 10 | 1 | 1(+0) | 2(+1) |
| Grade average |  | 1 | 1.2(+0.2) | 2(+0.8) |
| IFN-β-dextran administration 0.75 MIU/kg, 8 times | 1 | 0 | 1(+1) | 1(+0) |
|  | 2 | 1 | 2(+1) | 3(+1) |
|  | 3 | 1 | 1(+0) | 1(+0) |
|  | 4 | 4 | 4(+0) | 4(+0) |
| Grade average |  | 1.5 | 2(+0.5) | 2.25(+0.3) |

*The values in the parentheses are differences from the last Grades.

EXAMPLE 3

Sustained Distribution of IFN-β-Dextran Complex in Choroidal (Neovasculature Site) (Effect of Prolonging Duration in Blood)

Choroidal neovasculature models were prepared according to the method of Kimura et al. (Invest. Ophthalmol. Vis. Sci., 36 (10), 2110–2119, 1995). Namely, a gelatin microsphere containing 100 μg of a basic fibroblast growth factor (bFGF) was injected into the subretinal space of pigmented house rabbit eyes. Fluorescent fundus photography was carried out on the 21st day after the bFGF injection, and retinal neovascularization was confirmed. The crude IFN-β-dextran complex (7.5 MIU/kg/day) prepared in Example 1 or IFN-β (7.5 MIU/kg/day) was injected intravenously on the 22nd day after the bFGF injection. As a control group, physiological saline was administered similarly. Specimens of eye balls extirpated one day after the intravenous injection were immunostained with an anti-IFN-β antibody to measure degrees of distribution of IFN-β in choroidal (neovasculature site).

As a result, strong staining was observed in the choroidal (neovasculature site) only in the group to which the IFN-β-dextran complex had been administered, but no staining was observed in other groups.

The present IFN-dextran complex is characterized by improving stability of IFN in blood and acting specifically on tissues having neovasculature, particularly tumors or ophthalmic tissues having neovasculature (targeting) and facilitates extremely improvement of efficacy of IFN, particularly improvement of efficacy as an angiogenesis inhibitor.

INDUSTRIAL APPLICABILITY

The present invention relates to an interferon-dextran complex being a novel administration system of interferon, a process for producing the same, pharmaceutical use thereof and a method of prolonging duration of interferon in blood by forming the interferon-dextran complex. The present invention can provide modified IFN so that the duration of IFN in blood is prolonged and IFN acts specifically on tissues having neovasculature, particularly tumors or ophthalmic tissues having neovasculature.

What is claimed is:

1. An interferon-dextran complex which is obtained by mixing an interferon with a dextran having a chelate ligand, in the presence of a metal ion wherein the metal ion is at least one metal ion selected from the group consisting of a zinc ion, copper ion, a nickel ion and a cobalt ion.

2. The interferon-dextran complex as claimed in claim 1, wherein the interferon is interferon β.

3. The interferon-dextran complex as claimed in claim 1, wherein the chelate ligand is diethylenetriamine pentaacetic acid.

4. A pharmaceutical composition comprising the interferon-dextran complex as claimed in claim 1 as an active ingredient and a pharmacologically acceptable carrier or excipient.

5. A method of inhibiting angiogenesis comprising administering an effective amount of the interferon-dextran complex as claimed in claim 1 to a patient in need thereof.

6. A method of preparing an interferon for prolonging the duration of an interferon in the blood of a patient, the method comprising mixing an interferon with a dextran having a chelate ligand, in the presence of a metal ion to form an interferon-dextran complex wherein the metal ion is at least one metal ion selected from the group consisting of a zinc ion, copper ion, a nickel ion and a cobalt ion.

7. A process for producing an interferon-dextran complex comprising mixing an interferon with a dextran having a chelate ligand, in the presence of a metal ion wherein the metal ion is at least one metal ion selected from the group consisting of a zinc ion, copper ion, a nickel ion and a cobalt ion.

8. The interferon-dextran complex as claimed in claim 2, wherein the chelate ligand is diethylenetriamine pentaacetic acid.

9. A pharmaceutical composition comprising the interferon-dextran complex as claimed in claim 2 as an active ingredient and a pharmacologically acceptable carrier or excipient.

10. A pharmaceutical composition comprising the interferon-dextran complex as claimed in claim 3 as an active ingredient and a pharmacologically acceptable carrier or excipient.

11. A pharmaceutical composition comprising the interferon-dextran complex as claimed in claim 1 as an active ingredient and a pharmacologically acceptable carrier or excipient.

12. A pharmaceutical composition comprising the interferon-dextran complex as claimed in claim 8 as an active ingredient and a pharmacologically acceptable carrier or excipient.

13. A method of inhibiting angiogenesis comprising administering an effective amount of the interferon-dextran complex as claimed in claim 2 to a patient in need thereof.

14. A method of inhibiting angiogenesis comprising administering an effective amount of the interferon-dextran complex as claimed in claim 3 to a patient in need thereof.

15. A method of inhibiting angiogenesis comprising administering an effective amount of the interferon-dextran complex as claimed in claim 1 to a patient in need thereof.

16. A method of inhibiting angiogenesis comprising administering an effective amount of the interferon-dextran complex as claimed in claim 8 to a patient in need thereof.

17. The method of inhibiting angiogenesis according to claim 5, wherein said interferon-dextran complex is administered to a patient suffering from ophthalmopathy.

18. The method of inhibiting angiogenesis according to claim 17, wherein the interferon is interferon $\beta$; the chelate ligand is diethylenetriamine pentaacetic acid.

* * * * *